United States Patent [19]

Talwar et al.

[11] Patent Number: 5,501,855
[45] Date of Patent: Mar. 26, 1996

[54] NEEM OIL AS A MALE CONTRACEPTIVE

[76] Inventors: Gursaran P. Talwar; Shakti N. Upadhyay; Suman Dhawan, all of J.N.U. Complex, Shahid Jeet Singh Marg, New Delhi 110 067, Ind.

[21] Appl. No.: 115,867

[22] Filed: Sep. 2, 1993

[51] Int. Cl.$^6$ .......... A61K 35/78; A61K 31/335; A61K 31/34; A61K 31/12

[52] U.S. Cl. .......... 424/195.1; 514/450; 514/468; 514/680; 514/841

[58] Field of Search .......... 424/195.1; 514/450, 514/468, 680, 841

[56] References Cited

U.S. PATENT DOCUMENTS 5,196,197  3/1993  Talwar et al. .......... 424/195.1

*Primary Examiner*—Kimberly R. Jordan
*Attorney, Agent, or Firm*—Cooper & Dunham

[57] ABSTRACT

An alternate approach to vasectomy for long term male contraception following a single intra-vas.application of a traditional plant (Azadirachta indica) product having immunomodulatory properties is described. The intra-vas administration of neem oil to male rats resulted in a block of spermatogenesis without affecting the testosterone production; the seminiferous tubules, although reduced in diameter, appeared normal and contained mostly early spermatogenic cells. No antisperm antibody could be detected in the serum. Unilateral administration of neem oil in the vas resulted in a significant reduction of testicular size and spermatogenic block only on the side of application; the draining lymph node cells of the treated side also showed enhanced proliferative response to in vitro mitogen challenge. These results indicate that intra-vas application of neem oil is effective in blocking fertility in male mammals after a single injection.

7 Claims, 6 Drawing Sheets

NEEM OIL AS A MALE CONTRACEPTIVE

FIELD OF THE INVENTION

The present invention relates to a method for the control of fertility in males. In particular, the invention relates to the intra-vas administration of neem oil to the male resulting in a long term block in fertility.

BACKGROUND OF THE INVENTION

The neem tree (Azadirachta indica or Melia azadirachta) found throughout India and other countries has been reported to have various medicinal utilities. In particular, various parts of the tree have been utilized in the treatment of arthritis (Pillal and Santhakumari 1981), inflammation (Okpanyi and Ezeukwu 1981) and malaria (Obbaseki and Jeged-Fadunsin, 1986). Neem oil, also known as oil of Margosa, has been shown to possess anti-diabetic (Chakrabarty and Poddar, 1984) anti-bacterial (Singh and Sastry, 1981), anti-fungal (Kher and Chaurasia, 1977) and anti-fertility effects in the female (Talwar, U.S. Pat. No. 5,196, 197).

The realization of the anti-fertility effects of neem oil in the female animal was quite important especially in view of the problems with population control in most developing countries. Alternative forms of birth control are also desirable in industrialized countries due to the recognized problems associated with known contraceptives. However, most contraceptives are aimed at controlling fertility in the female which unfairly imposes sole responsibility for birth control on the female. One accepted method of contraception in the male has been a vasectomy. However, this procedure has been reported to give rise to problems related to the formation of anti-sperm antibodies and associated changes in the epididymis and testes. (Herr, et al 1987; Flicklnger et al 1990). Consequently, there is a real need to provide new methods for blocking fertility in the male.

SUMMARY OF THE INVENTION

The present invention relates to a new method for controlling fertility in male mammals. In particular, the invention demonstrates that neem oil is effective in inducing a long term block of fertility in males by a single intra-vas administration.

Accordingly, the present invention provides a method of blocking the fertility in a male mammal which comprises administering neem oil or an active component thereof into the vas deferens of the male in an amount sufficient to block the fertility of said male.

The present invention also provides a male anti-fertility agent comprising neem oil or an active component thereof in an amount sufficient to block fertility in a male mammal.

The block in fertility has been demonstrated to be reversible, lasting from about 5 to about 11 months after a single intra-vas inject ion of neem oil.

EXAMPLE 1

Figure 1:
FIG. 1: Photomicrograph of a portion of cauda epididymis of a rat 4 weeks after intra-vas administration of peanut oil. Note normal morphology of the ducts and the presence of spermatozoa in the ductular lumen. X 250

The following example is provided to illustrate the present invention. The invention is not meant to be restricted thereto. The example demonstrates thay neem oil is effective in blocking fertility in male rats.

MATERIAL AND METHODS

ANIMALS,

Male Wistar rats of proven fertility were used in this study. Animals were maintained under standard laboratory conditions. Water and dry pellet diet were given ad libitum.
NEEM OIL, Neem oil was expressed from decorticated kernels of Azadirachta indica by mechanical expeller at ambient temperature and centrifuged to remove particulate material. The oil was used within 3 months of extraction since it is known to loose its biological activity following longer storage and exposure to light.

SURGICAL PROCEDURES,

Surgical procedures were carried out under anaesthesia (intra-peritoneal injection of 1 ml of 1% avertin, 2,2,2-tribromomethanol in tertiaryamyl alcohol). The vas deferens was exposed through a midline incision on the lower abdomen; 50 ul of neem oil (or peanut oil) was administered into the lumen of the vas using a 26 gauge needle fitted to a glass syringe; initially the procedure was standardized by injecting India ink into the vas. The incision was closed using autoclips. There was no mortality due to the surgical procedure and the animals revived quickly.

FERTILITY STUDIES:

All animals were caged with females (1,2) of proven fertility, 4 weeks after surgery. Mating studies were continued for 8 months females were changed after every 3 estrous cycles. Vaginal smears were taken daily for monitoring sperm positivity, reproductive cyclicity and pregnancy; pregnancies were documented by delivery of pups.

SERA SAMPLES:

Blood samples were collected from orbital plexus for measurement of testosterone and anti-sperm antibody titres, before and at weekly intervals following the treatment. The serum was separated and stored at $-20°$ C. until assayed.

HISTOLOGY:

Some animals were sacrificed at 2, 4 and 6 weeks after the treatment, the remaining at the end of the fertility studies. Testis along with epididymis and vas deferens was dissected out; testicular weight was recorded and the tissue samples were immediately fixed in a solution containing 4% paraformaldehyde and 2.5% glutaraldehyde in 0.1M cacodylate buffer for 4–6 hours at $4°$ C. Samples were post-fixed in 1% osmium tetroxide, dehydrated in graded series of ethanol and embedded in epon-araldite. Semithin serial sections, stained with toluidine blue, were studied under a Zeiss Axiophot photomicroscope.

TESTOSTERONE ASSAY:

Testosterone levels in individual serum samples were determined according to the method described by Brenner et al (1973).

ANTI-SPERM ANTIBODY ASSAY:

Anti-sperm antibody titre in the serum samples was determined by ELISA as described by Herr et al (1986). Serum from a sperm-immunized rat was used as positive control. All sera were diluted 1:10, 1,50 and 1,100 for the assay, and the results were plotted as mean OD values at 1.50 dilution for all samples.

LYMPHOCYTE PROLIFERATION ASSAY:

Para-aortic and inguinal lymph node cells from experimental and control groups were isolated, washed and suspended in RPMI containing 10% fetal calf serum at a concentration of $5 \times 10^6$ cells/ml. One hundred microliters of this suspension were plated in 96-well plates and cultured for 72 hours with 100 ul of Con A (5 ug/ml); controls without Con A were maintained. $^3$H-Thymidine (1 uCi) was added to each well and the cells were harvested after 18 hours; thymidine incorporation was measured using a beta counter (Phamacia). All tests were done in triplicate.

RESULTS

A group of 10 animals were given 50 ul of neem oil in the vas deferens of each side; a control group of equal numbers received the same volume of peanut oil on both sides. Animals were put on continuous mating with females of proven fertility, 4 weeks after the treatment. The results showed that administration of peanut oil in the vas did not affect fertility, all animals of this control group could impregnate their female partners. The animals treated with neem oil, however, remained infertile during the 8 month period of observations none of the females caged with neem oil treated males showed sperm positive mating. The treatment, however, did not affect libido and mating since the females frequently manifested pseudo-pregnancy for 10–12 days as evidenced by prolonged diestrous stage. The control animals impregnated females within first or second cycle.

Figure 2:
FIG. 2: Photomicrograph of a portion of cauda epididymis of a rat, 4 weeks after intra-vas administration of neem oil. Note normal morphology of the ducts without any evidence of inflammatory reaction and the absence of sperm in the ductular lumen. X 250
Figure 3:
FIG. 3: Photomicrograph of a section through vas deferens of a rat, 4 weeks after intra-vas administration of peanut oil, showing normal morphology and the presence of sperm in the lumen. X 250
Figure 4:
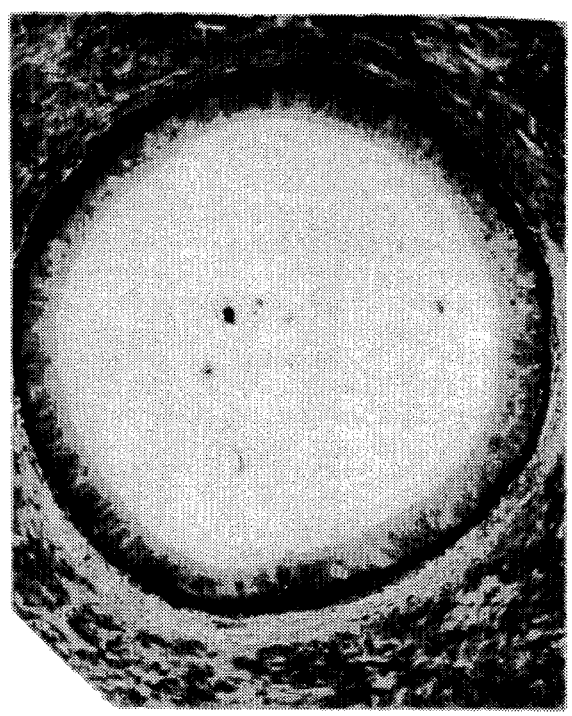
FIG. 4: Photomicrograph of a section through vas deferens of a rat, 4 weeks after intra-vas administration of neem oil, showing normal morphology without any evidence of inflammatory reaction and the absence of sperm in the lumen. X 250
Figure 5:
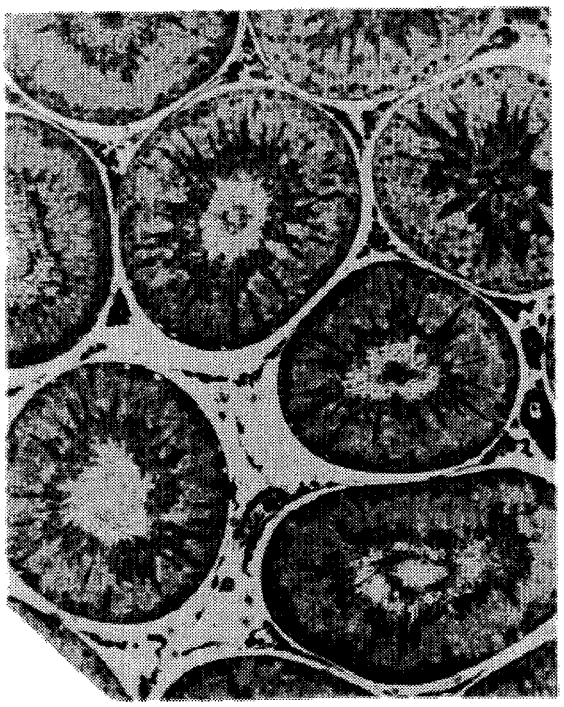
FIG. 5: Photomicrograph of a portion of testis of rat, 4 weeks after intra-vas administration of peanut oil, showing normal morphology of the seminiferous tubules+X 100

Histological appearance of epididymis and vas was normal following application of neem oil (FIGS. 1–4). The lumen of excurrent ducts was, however, devoid of spermatozoa by 4 weeks of treatment (FIGS. 2 & 4). No occlusion, granuloma or inflammatory changes were noted in the vas and epididymis; the lumen was patent and the epithelial cells lining the ducts had normal morphology (FIGS. 2 & 4).

Figure 7:
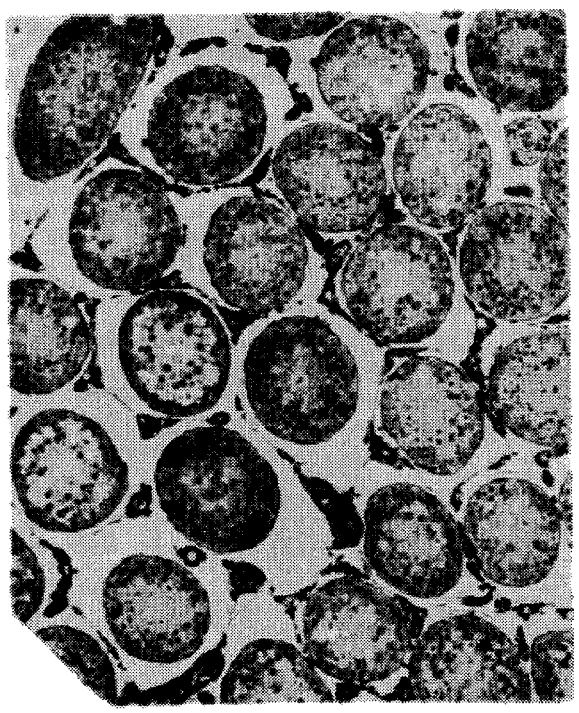
FIG. 7: Photomicrograph of a portion of testis of rat, 4 weeks after intra-vas administration of neem oil, showing significant reduction in seminiferous tubule diameter and the arrest of spermatogenic process. X 100
Figure 6:
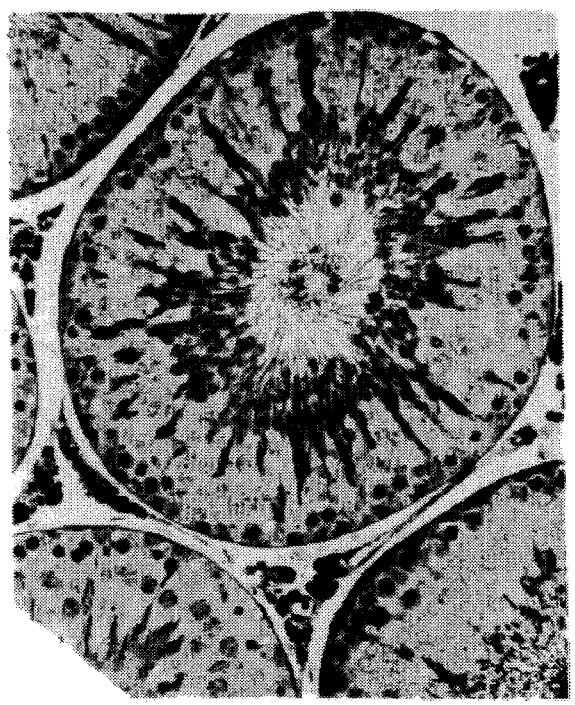
FIG. 6: Higher 6 magnification of FIG. 5, showing seminiferous tubules. Normal spermatogenesis can be noted in the seminiferous epithelium. X 200
Figure 8:
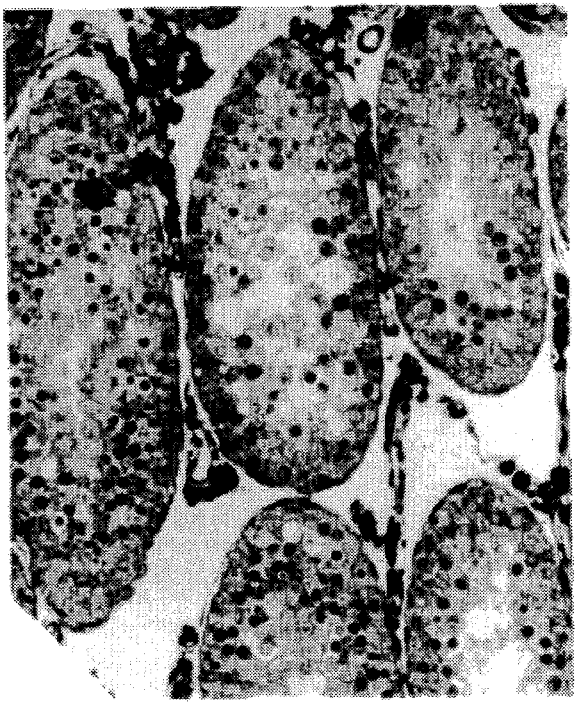
FIG. 8: Higher magnification of the Same testis shown in FIG. 7: showing the presence of early spermatogenic cells in the seminiferous tubules. No leukocytic infiltration is seen in the interstitial space. X 200

Histological studies on testes revealed that by intra-vas application of neem oil, spermatogenesis was impaired as early as two weeks after the treatment. By 4 weeks, a drastic reduction of seminiferous tubule diameter and complete block in spermatogenesis was noted (FIGS. 5–8); the seminiferous tubules contained mainly spermatogonia and primary spermatocytes (FIGS. 7 & 8). The Leydig cells, however, appeared normal. There was no leukocytic infiltration in the testicular interstitium. The block of spermatogenesis was observed even after 9 months of treatment; the seminiferous tubules, however, did not show any sign of degeneration or resorption and still contained a few spermatogonia.

Figure 9:
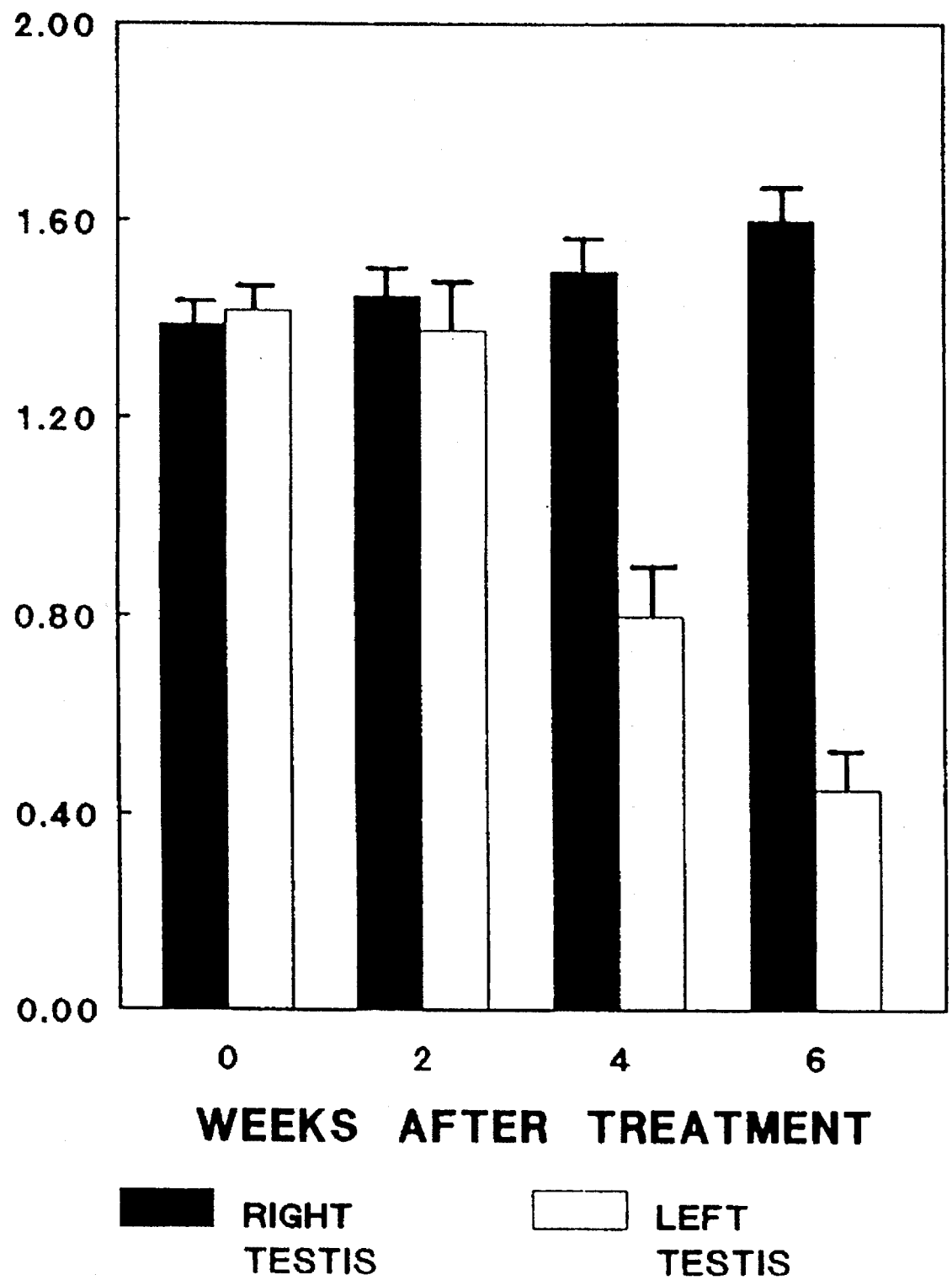
FIG. 9: Effect of unilateral (left side) intra-vas administration of neem oil on the testicular weight in rats. The values are expressed as mean S. E. M. Note the significant reduction ($P<0.01$) of the testicular weight by 6 weeks after treatment.

Unilateral administration of neem oil in the vas had a similar effect on testis but only on the side of treatment. While the testicular weight of the control side remained unaffected, the treated side showed a significant reduction ($P<0.01$) in gross weight by 6 weeks of treatment (FIG. 9). The block in spermatogenesis was also noted only on the treated side.

Figure 10:
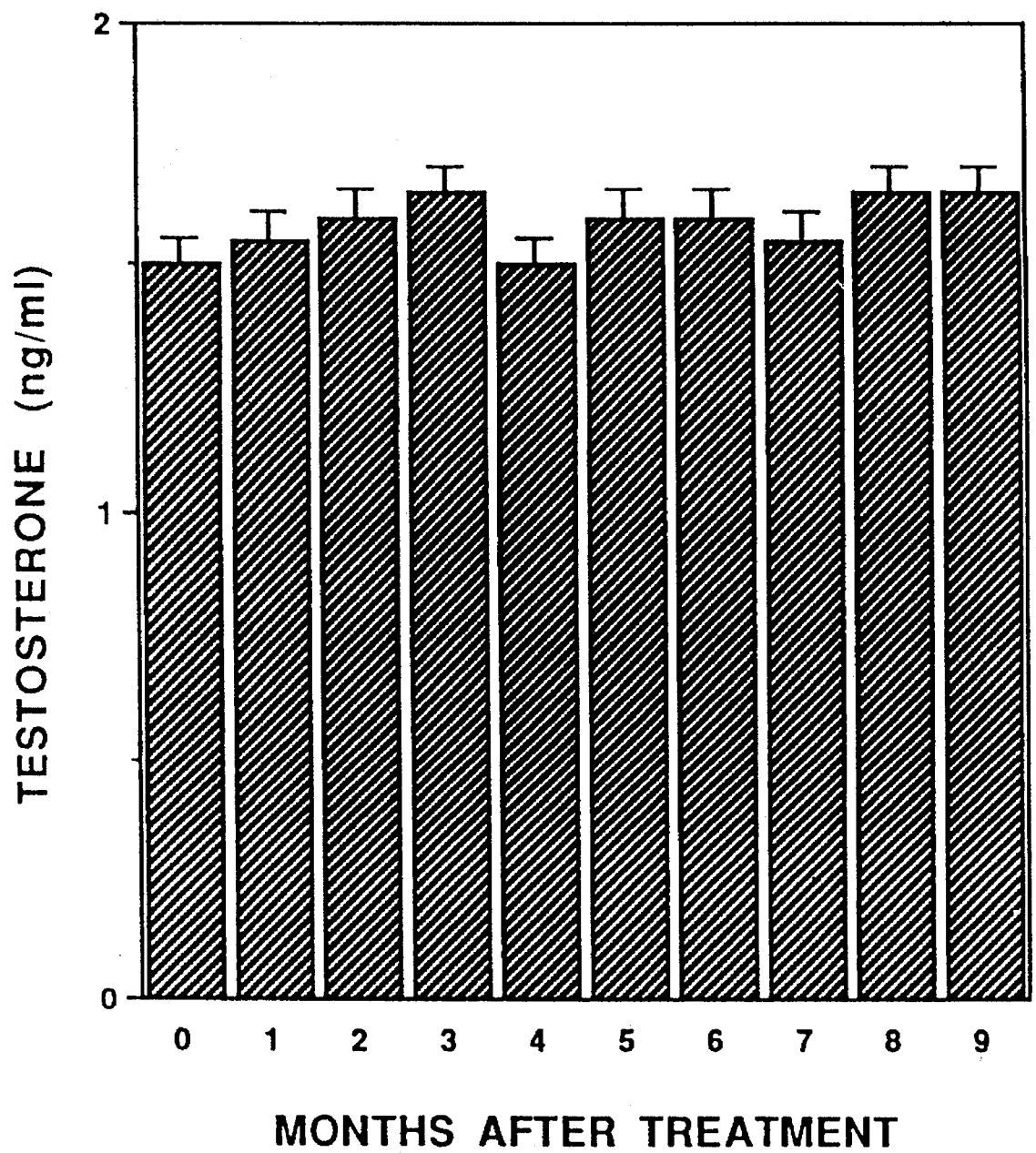
FIG. 10. Testosterone levels in rats following intra-vas treatment with neem oil showing normal profile up to 9 months.
Figure 11:
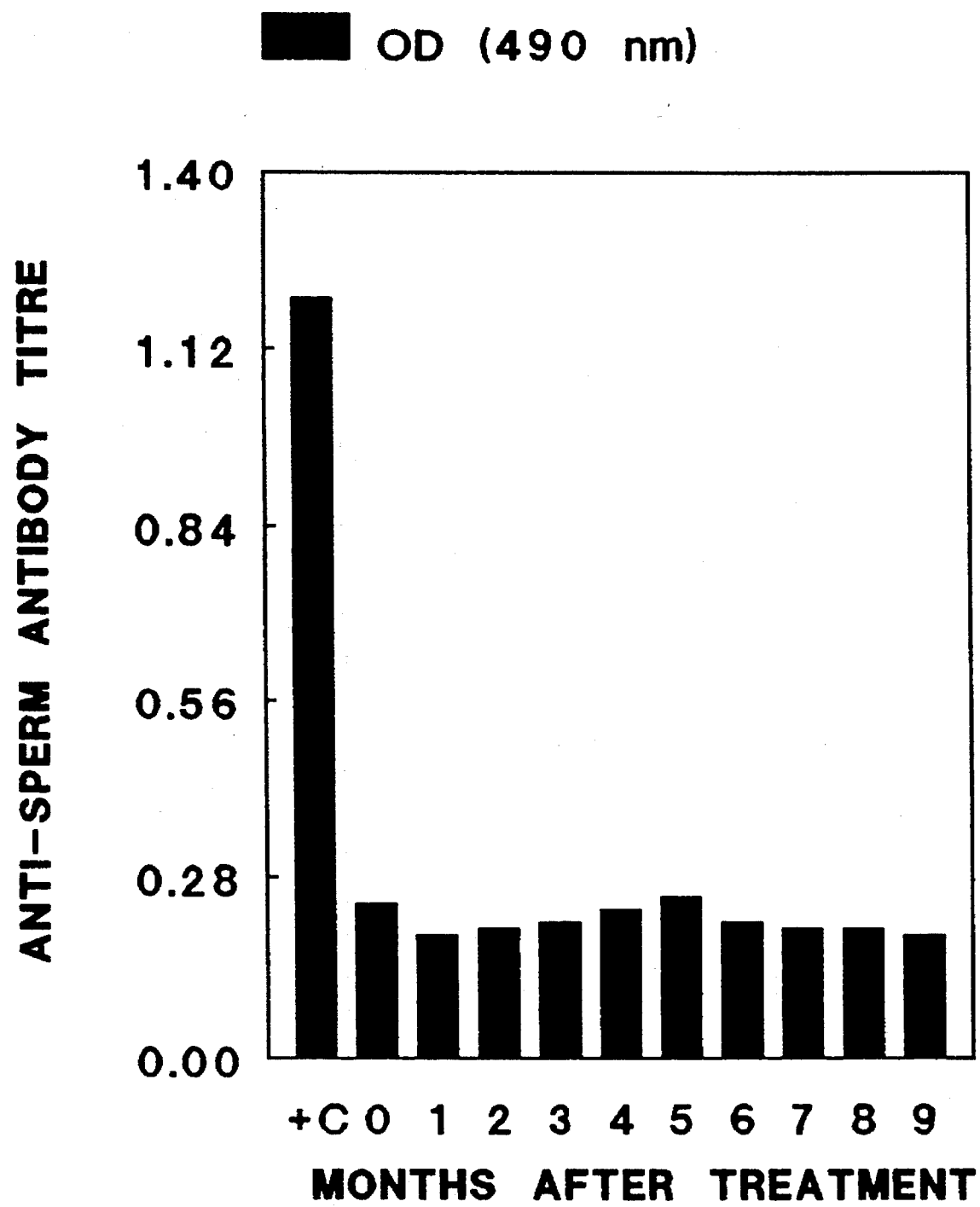
FIG. 11. ELISA values for anti-sperm antibody in rats, up to 9 months, following intra-vas administration of neem oil. Titres are expressed as mean optical density (OD) values at sera dilution of 1,50; serum from a sperm-immunized male rat was used as a positive control (-C).

Serum testosterone levels, as shown in FIG. 10, indicated that the bilateral intra-vas administration of neem oil did not affect the endocrine functions of the testes; the testosterone levels were comparable to that in control animals. No anti-sperm antibodies could be detected in serum of neem oil treated animals (FIG. 11).

Figure 12:
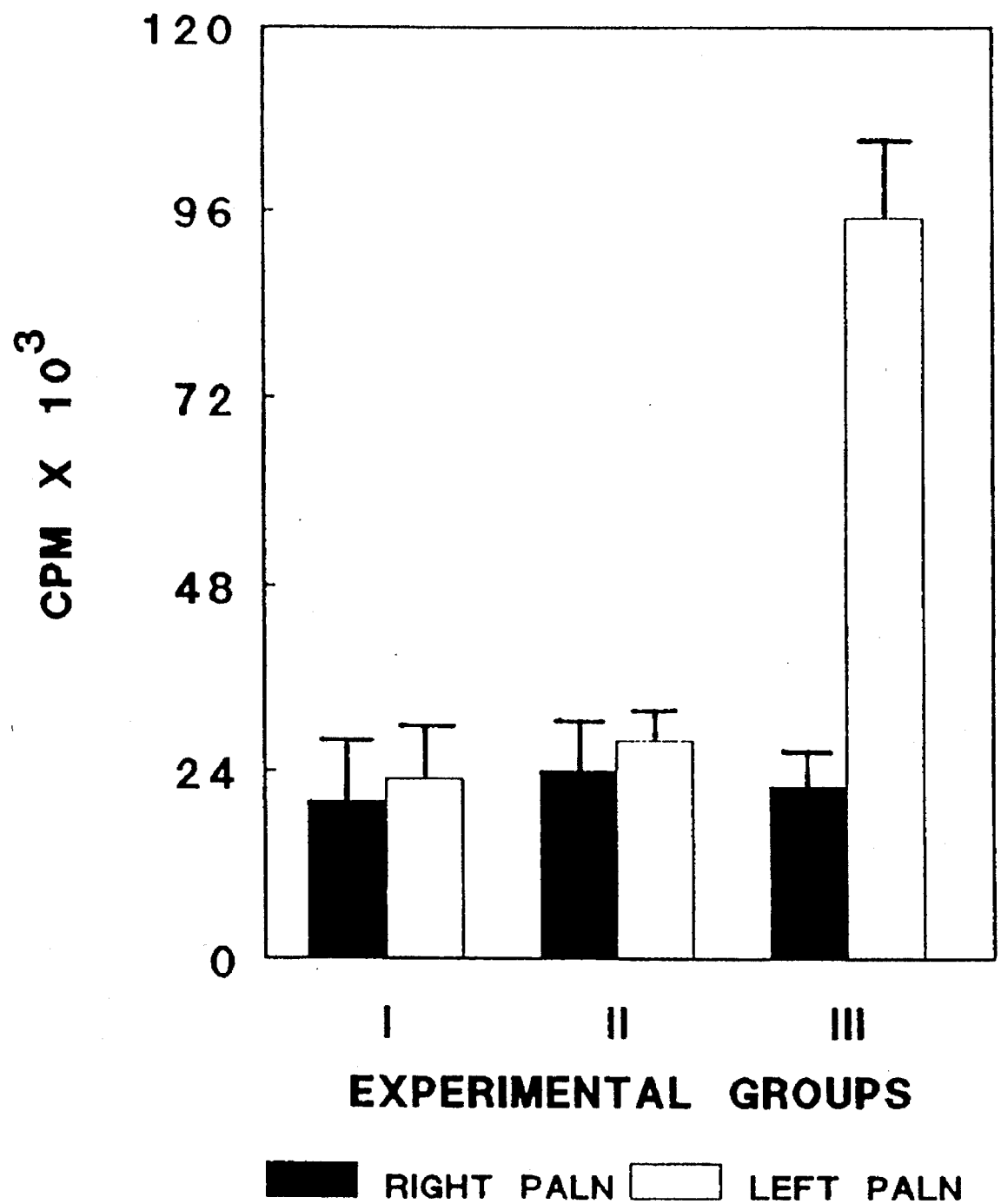
FIG. 12. Lymphocyte proliferative response of regional lymph node cells to in vitro challenge with Concanavalin A (Con-A) (5 ug/ml) for 72 hours as measured by $3_H$-thymidine incorporation. The values are expressed as mean S. E. M. Experimental groups I, II and III represent animals receiving saline, peanut oil and neem oil in the left vas deferens, respectively, in all groups, right vase was left untreated. In Group III, a significant ($P<0.001$) increase in lymphocyte proliferative response to Con-A was noted in the lymph node cells of the treated side as compared to that of the contralateral untreated side. No significant difference was noted between the two sides in the control groups, I and II.

The effect of intra-vas administration of neem oil on the regional draining lymph nodes (para-aortic and inguinal) was studied in order to understand the localized effect following unilateral treatment. Three experimental groups of six animals each were given saline, peanut oil and neem oil, respectively, into the left vas; in all groups, the right vas, was left untreated. The lymph nodes of both sides were removed after 2 weeks and were challenged in vitro with Con-A (5 ug/ml). The results, shown in FIG. 12, indicate that in Group III, the lymph node cells of the treated side show significantly higher response ($P<0.001$) to Con-A as compared to that of the contralateral side; the two control groups (I and II) had no difference between the response of left and right side.

DISCUSSION

This example demonstrates that a single administration of neem oil in the vas induces a long term block of fertility of male rats. The treatment does not lead to any inflammatory reaction or occlusion in the vas or epididymis; in fact, In Indian traditional medicine, neem oil is known for its antiinflammatory properties and this has been confirmed by recent experimental studies (Labadie et al, 1989). The long term anti-fertility effect as noted in the present study appears to be due to the arrest of spermatogenesis. It is possible that the block of fertility nay be reversible since the spermatogenic stem cells, the spermatogonia, were still present in the seminiferous tubules after 9 months of treatment. Intra-vas treatment with neem oil did not affect testosterone production or libido. The animals continued to mate normally as evidenced by induction of pseudo-pregnancy in females for 10 to 12 days, a phenomenon well known to occur in rodents after infertile mating. The treatment did not lead to formation of anti-sperm antibodies. The block of spermatogenesis does not seem to be mediated by any systemic mechanism since the unilateral administration of neem oil affected only the test is of that side; a systemic involvement would have affected testes of both sides.

The mechanism of long term spermatogenic arrest following a single application of neem oil in the vas may possibly be mediated by local cell mediated immune mechanisms. This study demonstrates that unilateral intra-vas application of neem oil activates the immune cell population in the draining lymph nodes of the treated side, which show enhanced response to mitogenic challenge, whereas the lymph nodes of untreated contralateral side show normal response. The inventors have earlier demonstrated that neem oil possesses immuno-stimulatory properties and that it non-specifically activates the immunocompetent cells. In particular, it enhances the phagocytic and antigen presenting ability of the macrophages (Upadhyay et al, 1992). Neem oil also induces production of gamma interferon (Upadhyay et al, 1992), an important mediator of cellular immune responses. Intra-vas administration of neem oil may activate the immuno-competent cells in the regional draining: lymph nodes. Recent reports suggest that the cytokines produced locally may be involved in the regulation of spermatogenic process (Pollanen et al, 1990). Although the precise role of these cytokines in the regulation of spermatogenesis is not clear, intra-vas treatment with neem oil may possibly interfere with normal production of the immune cell products necessary for the maintenance of the spermatogenic process.

The intra-vas application of neem oil for inducing long term block of fertility, without loss of androgens and libido, could serve as an alternate to vasectomy. Although vasectomy has been widely accepted for male contraception, it does give rise to problems related to formation of anti-sperm antibodies and associated inflammatory changes in the epididymis and testes (Herr et al, 1987; Flickinger et al, 1990). The procedure for administration of neem oil in the vas may be relatively easier and less traumatic than ligation and incision of the vas. The vas deferens is a convenient site for administration. Non-surgical techniques for intra-vas injections have been worked out and are practised in some countries such as China and India. The anti-inflammatory and anti-microbial properties of neem oil may be an added advantage during post-surgical recovery.

While the above example describes the ability of neem oil to block fertility in the male rat, it would be reasonable to predict that the same effect would be observed in other mammals such as humans and monkeys. Experiments are currently underway in the monkey using a dose of 0.2 to 0.5 ml. It is predicted that an effective dose in humans would be approximately up to 2 ml. It is also predicted that the anti-fertility effect would be reversible in all mammals.

REFERENCES

Brenner PF, Guerrero R, Cekan Z, Diczfalusy E. "Radioimmunassay method for sex steroids in human plasma." Steroids (1973) 22: 775–794

Chakrabarty T, Poddar G. Herbal drugs in diabetes. Part I. "Hypoglycaemic activity of indigenous plants in sterptozoticin induced diabetic rats". J. Inst. Chem., (1984) 56: 20–22.

Flickinger CF, Herr JC, Caloras D, Sisak JR, Howards SS. "Inflammatory changes in the epididymls after vasectomy in the Lewis rat." Bio Reprod (1990) 43, 34–45. Herr JC, Flickinger CJ, Howards SS, Yarbro S, Spell DR, Caloras D, Gallien TN. "An enzyme-linked immunosorbent assay for measuring antisperm autoantibodies following vasectomy in Lewis rats." Am J Reprod Immunol Microbiol (1986) 11: 75–81.

Herr JC, Flickinger CJ, Howards SS, Caloras D, Yarbro ES, Spell DR, Gallien TN. "The relation between antisperm antibodies and testicular alternations after vasectomy and vasovasotomy in Lewis rats." Bio Reprod (1987) 37: 1297–1305.

Kher A, Chaurasia SC. "Anti-fungal activity of essential oils of three medicinal plants Indian Drugs" (1977) 15:41–42.

Labadie RP, Van der Nat JM, Simons JM, Kroes BH, Van der Berg AJJ, Hart LA, Van der Sluis WG. "Advances in immunomodulating agents from medicinal plants and traditional preparations." Proc Sixth Asian Symp Med Plants and Spices, Bandung, Indonesia. (1989) 408–428.

Obaseki AO, Jegede-Fadunsin H.A. "Anti-malarial activity of Azadirachta indica". Filoterapia, (1986) 57: 247–251.

Okapanyi SN, Ezeukwu G.C. "Anti-inflamatory and anti-pyretic activities of Axaridachta india". Planta Med., (1981) 41:34–39.

Pillai NR, Santhakumari G. "Anti-arthritic and anti-inflamatory actions or nimbidin". Planta Med., (1981a) 43, 59–63.

Pollanen P, von Euler M, Soder O, 1990. "Testicular immunoregulatory factors." J Reprod Immunol (1990) 18: 51–76.

Singh N. Sastry MS, "Anti-microbia activity of neem oil." Indian J. Pharmacol., ( 1981 ) 13:102.

Sinha KC, Riar SS, Tiwary RS, Dhawan AK, Bardhan J, Thomas P, Kain AK, Jain RK. "Neem oil as a vaginal contraceptive." Indian J Med Res (1984) 79; 131–135.

Upadhyay SN, Dhawan 8, Garg S, Talwar GP. "Immunomodulatory effects of neem (Azadirachta indica) oil." Int J Immunopharmacol. (1992) 14:1187–1193.

We claim:

1. A method of blocking the fertility in a male mammal which comprises administering neem oil into the vas deferens of the male in an amount sufficient to block the fertility of said male.

2. A method according to claim 1 wherein said block in fertility is reversible.

3. A method according to claim 1 wherein said neem oil is administered in an amount sufficient to block fertility for about 5 to about 11 months.

4. A method according to claim 3 wherein said block in fertility is for about 8 months.

5. A method according to claim 1 wherein said male mammal is a human.

6. A method according to claim 5 wherein the neem oil is administered in a dosage of up to 2 milliliters.

7. A method according to claim 1 wherein said neem oil is administered as a single dose.

* * * * *